US006730815B2

(12) United States Patent
Baimbridge et al.

(10) Patent No.: US 6,730,815 B2
(45) Date of Patent: May 4, 2004

(54) METHOD OF PRODUCING GLYCOL ETHERS

(75) Inventors: Charles L. Baimbridge, Baton Rouge, LA (US); Pascal V. Bolomey, Solon, OH (US); James D. Love, Hudson, OH (US)

(73) Assignee: Ferro Corporation, Cleveland, OH (US)

( * ) Notice: Subject to any disclaimer, the term of this patent is extended or adjusted under 35 U.S.C. 154(b) by 97 days.

(21) Appl. No.: 10/229,938

(22) Filed: Aug. 28, 2002

(65) Prior Publication Data

US 2004/0044253 A1 Mar. 4, 2004

(51) Int. Cl.[7] .......................... C07C 41/44; C07C 43/04
(52) U.S. Cl. ..................................................... 568/679
(58) Field of Search ......................................... 568/679

(56) References Cited

U.S. PATENT DOCUMENTS

| 4,321,413 A | 3/1982 | Vanderpool |
| 4,360,698 A | 11/1982 | Sedon |
| 4,368,337 A | 1/1983 | Tawara et al. |
| 4,409,403 A | 10/1983 | Vaughan |
| 4,504,685 A | 3/1985 | Vaughan |
| 4,687,755 A | 8/1987 | Green |
| 4,762,952 A | 8/1988 | Green |
| 5,349,110 A | 9/1994 | Knifton |
| 5,994,595 A | 11/1999 | Onda et al. |

FOREIGN PATENT DOCUMENTS

DE 3446488 A1 7/1986

*Primary Examiner*—Taofiq A. Solola
(74) *Attorney, Agent, or Firm*—Rankin, Hill, Porter & Clark LLP

(57) ABSTRACT

The present invention provides a method of producing glycol ethers, which are also commonly known as glymes. The method according to the invention includes contacting a glycol with a monohydric alcohol in the presence of a polyperfluorosulfonic acid resin catalyst under conditions effective to produce the glyme. The method of the invention can be used to produce, for example, monoglyme, ethyl glyme, diglyme, ethyl diglyme, triglyme, butyl diglyme, tetraglyme, and their respective corresponding monoalkyl ethers. The present invention also provides a method of producing 1,4-dioxane from mono- or diethylene glycol and tetrahydrofuran from 1,4-butanediol.

22 Claims, No Drawings

METHOD OF PRODUCING GLYCOL ETHERS

BACKGROUND OF THE INVENTION

1. Field of Invention

The present invention relates to a method of producing glycol ethers.

2. Description of Related Art

Glycol ethers, which are also commonly known as glymes, are used as aprotic solvents in a variety of applications. Glymes can be produced by a variety of methods, but are conventionally produced in commercial quantities via the Williamson synthesis or via a reaction that involves the cleavage of epoxides.

In the Williamson synthesis, a monoalkyl polyalkylene glycol is treated with a base or an alkali metal, typically molten sodium, to form an alkoxide ion, which is then reacted with an alkyl halide such as methyl chloride to form the glyme. The by-products from the Williamson synthesis are hydrogen gas and a salt.

Although the Williamson synthesis is one of the conventional methods of producing glymes on a commercial scale, the process presents several disadvantages. For example, the Williamson synthesis requires the use of costly and potentially hazardous starting materials. It generates hydrogen gas as a by-product, which presents safety and handling issues. Moreover, for every mole of glyme produced, the process generates a mole of salt as a by-product, which presents treatment and disposal issues. Furthermore, the Williamson synthesis proceeds at a relatively slow rate.

The other conventional method for commercially producing glymes involves the cleavage of epoxides in presence of a low molecular weight ether and a Lewis acid catalyst. This reaction enables the insertion of oxacycloalkanes into chain-type ethers. A typical reaction involves dimethyl ether and ethylene oxide with catalytic amount of boron trifluoride or boron trifluoride dimethyletherate to yield, among other ether co-products, monoethyleneglycol dimethylether.

One of the principle disadvantages of the cleavage reaction of epoxides is that it is not particularly selective. Insertion of a specific number of oxacycloalkane units is difficult to control. Therefore, the final product consists of a mixture of glymes. It is necessary to separate the reaction mixture by complex distillation techniques or by other means in order to obtain pure glymes, which adds time and complexity to the manufacturing process.

BRIEF SUMMARY OF THE INVENTION

The present invention provides a method of producing glymes that overcomes the disadvantages of both the Williamson synthesis and the cleavage reaction of epoxides. The method according to the invention comprises contacting a glycol with a monohydric alcohol in the presence of a polyperfluorosulfonic acid resin catalyst under conditions effective to produce the glyme. The starting materials used in the method according to the invention are commercially readily available, not expensive or hazardous, and the catalyst used in the reaction can be recovered, regenerated, and reused. The method according to the invention does not generate hydrogen gas or salt, it proceeds at a relatively rapid rate, and it produces a single glyme.

The foregoing and other features of the invention are hereinafter more fully described and particularly pointed out in the claims, the following description setting forth in detail certain illustrative embodiments of the invention, these being indicative, however, of but a few of the various ways in which the principles of the present invention may be employed.

DETAILED DESCRIPTION OF THE INVENTION

Glymes are produced in accordance with the method of the invention by contacting a glycol with a monohydric alcohol in the presence of a polyperfluorosulfonic acid resin catalyst under conditions effective to produce the glyme. A wide range of glymes can be produced in accordance with the invention, with the resulting glyme being dependent upon the glycol and monohydric alcohol selected for use in the reaction.

For example, ethylene glycol and methanol react in accordance with the method of the invention to produce ethylene glycol dimethyl ether (monoglyme). These two reactants also react to produce ethylene glycol monomethyl ether, which is also known as 2-methoxyethanol or "Methyl CELLOSOLVE®". CELLOSOLVE® is a trademark of the Dow Chemical Company used in connection with a class of ethylene glycol monoalkyl ethers.

Ethylene glycol and ethanol react in accordance with the method of the invention to produce ethylene glycol diethyl ether (ethyl glyme). These two reactants also react to produce ethylene glycol monoethyl ether, which is also known as 2-ethoxyethanol or "Ethyl CELLOSOLVE®".

Diethylene glycol and methanol react in accordance with the method of the invention to produce diethylene glycol dimethyl ether (diglyme). These two reactants also produce diethylene glycol monomethyl ether, which is also known as methoxyethoxy ethanol or "Methyl CARBITOL®". CARBITOL® is a trademark of the Dow Chemical Company used in connection with a class of diethylene glycol monoalkyl ethers.

Diethylene glycol and ethanol react in accordance with the method of the invention to produce diethylene glycol diethyl ether (ethyl diglyme). These two reactants also produce diethylene glycol monoethyl ether, which is also known as "Ethyl CARBITOL®".

Diethylene glycol and 1-butanol react in accordance with the method of the invention to produce diethylene glycol dibutyl ether (butyl diglyme). These two reactants also produce diethylene glycol monobutyl ether, which is also known as "Butyl CARBITOL®".

Triethylene glycol and methanol react in accordance with the method of the invention to produce triethylene glycol dimethyl ether (triglyme). These two reactants also produce triethylene glycol monomethyl ether, which is also known as methoxytriglycol.

Tetraethylene glycol and methanol react in accordance with the method of the invention to produce tetraethylene glycol dimethyl ether (tetraglyme). These two reactants also produce tetraethylene glycol monomethyl ether, which is also known as methoxytetraglycol. It will be appreciated that other glymes can be produced in accordance with the method of the invention simply be selecting other glycols and monohydric alcohols.

The starting materials used in the reaction, being glycols and monohydric alcohols, are generally inexpensive and readily available. These starting materials do not present significant toxicity and handling problems, especially when compared to the starting materials used in the Williamson synthesis.

Preferably, a molar excess of the monohydric alcohol is used in the reaction. Typically, a molar excess of about 3 to about 5 moles of monohydric alcohol is used in the reaction for every mole of glycol.

The polyperfluorosulfonic acid resin catalyst used in the method of the invention is a Bronsted acid, and not a Lewis acid. Suitable polyperfluorosulfonic acid resins are available from E.I. Du Pont de Nemours and Company under the NAFION® trademark. These polyperfluorosulfonic acid resins are believed to be copolymers of tetrafluoroethylene and perfluoro-3,6-dioxa-4-methyl-7-octenesulfonyl fluoride, which have been converted to the proton ($H^+$) form. They are available in flake, pellet, powder, film, and solution form. The polyperfluorosulfonic acid resin catalyst is preferably used at about 0.5 to about 2.0 equivalents per 100 moles of glycol, with about 1.0 equivalent being most preferred during the preparation of monoglyme. The polyperfluorosulfonic acid resin catalyst is nearly solubilized during the reaction, and appears to act as a homogeneous catalyst.

In accordance with the preferred embodiment of the invention, the glycol, the monohydric alcohol, and the polyperfluorosulfonic acid resin catalyst are combined in a suitable reactor vessel under agitation and heated. Due to the high vapor pressures of the reactants and the products formed during the reaction, the reactor vessel must be capable of handling pressures as high as 1,000 psig (the term "psig" means pounds per square inch above atmospheric pressure, i.e., gauge pressure). A conventional autoclave is a preferred reactor vessel for use in accordance with the invention.

An elevated reaction temperature allows the catalyst to partially dissolve in the reaction mixture, thus providing semi-homogeneous catalysis conditions. For the production of glymes, a reaction temperature in the range of 100° C. to 300° C., preferably between 160° C. and 220° C. is suitable. Specifically for monoglyme and diglyme, the reaction temperature is selected most preferably between 190° C. and 210° C.

The reaction proceeds at a relatively rapid rate, at least as compared to the rate of the Williamson synthesis. For the synthesis of glymes, a reaction time ranging from about 0.5 hours to about 10 hours is typically sufficient, with 3 to 6 hours being preferred. A reaction time of from between 4 and 5 hours is most preferred for the production of monoglyme and diglyme.

Once the reaction has been completed, the reactor contents are cooled to ambient temperatures and the reactor contents are separated by distillation. As noted above, in addition to the formation of the desired products such as monoglyme, ethyl glyme, diglyme, ethyl diglyme, triglyme, butyl diglyme, and tetraglyme, the method also produces a quantity of the corresponding intermediate monoalkyl ether (i.e., 2-methoxyethanol, 2-ethoxyethanol, methoxyethoxy ethanol, diethylene glycol monoethyl ether, methoxytriglycol, diethylene glycol monobutyl ether, and methoxytetraglycol, respectively). These materials can easily be separated and recovered by conventional distillation to be recycled in the process to achieve further conversion. In the case of diglyme production, 1,4-dioxane is formed as a co-product.

By-products from the reaction include water and dialkyl ethers, which are also easily separated and recovered by distillation. Dialkyl ethers such as dimethylether are high value products, and can be used in a variety of applications.

The polyperfluorosulfonic acid resin catalyst can also be recovered in concentrated form in the glycol bottoms for reuse in accordance with known methods. Once the activity of the polyperfluorosulfonic acid declines, the material can be regenerated by treatment with a strong mineral acid (i.e. nitric acid) to restore the proton sites on the resin. The glycol bottoms are further stripped off residual lights to yield a concentrated polyperfluorosulfonic acid resin catalyst solution. The later is transferred into a dryer, typically a double-cone dryer, to evaporate the remaining liquid constituents. The resulting solid can then be treated in a separate vessel with a strong mineral acid (i.e. nitric acid) at 80° C. for 1 hour. After several washes, the regenerated polyperfluorosulfonic acid resin catalyst is dried and recycled in the process.

It will be appreciated that the reaction described above can also be performed by continuously feeding the glycol, monohydric alcohol and polyperfluorosulfonic acid resin into a reactor, while maintaining all operating conditions within a reaction zone within the reactor constant. The continuous feed may consist of fresh reactants, recycled unreacted reactants, intermediates or combinations of two or more thereof.

One of the advantages of the method of the present invention is that the reaction can be performed in conventional stainless steel reactor vessels, which is not practical in prior art sulfuric acid catalyzed reactions. Sulfuric acid, while inexpensive, is difficult to handle and tends to heavily carbonize and corrode stainless steel reactor vessels. Moreover, sulfuric acid is a one-time-use catalyst that cannot be effectively recycled. In addition, the yields and selectivity of sulfuric acid catalyzed reactions are poor as compared to the method of the present invention. Finally, sulfuric acid catalyzed reactions tend to produce darkly colored products, which are avoided in accordance with the present invention.

It is possible to form useful compounds other than glymes in accordance with the invention. For example, reacting ethylene glycol with itself in the presence of a polyperfluorosulfonic acid resin catalyst will produce 1,4-dioxane. Similarly, reacting 1,4-butanediol with itself in the presence of a polyperfluorosulfonic acid resin catalyst will produce tetrahydrofuran. Other useful compounds can also be produced in this manner.

The following examples are intended only to illustrate the invention and should not be construed as imposing limitations upon the claims.

EXAMPLE 1

186 grams (3.0 moles) of ethylene glycol, 384 grams (12.0 moles) of methanol, and 17 grams (0.015 equivalents) of NAFION® 1100 EW Polymer ($H^+$ form) were charged to a one-liter autoclave. After sealing and pressure testing, the contents of the autoclave were agitated and the autoclave was pressurized to 100 psi with nitrogen. After 5 minutes of agitation, the autoclave was depressurized. This process was repeated two more times to assure complete deoxygenation.

After deoxygenation, the autoclave was heated to a temperature of 198° C. and the contents of the autoclave were agitated at 1900 rpm for 5 hours at temperature (198–200° C.). A pressure of 930 psi was obtained. After 5 hours, the autoclave was cooled and sampled.

By analysis, a total of 75.7% by weight of the ethylene glycol (2.27 moles) was converted during the reaction, producing 0.639 moles of monoglyme and 1.50 moles of the intermediate ethylene glycol monomethylether (2-methoxyethanol) for a combined yield of 71.4% and selectivity of 94.3%.

EXAMPLE 2

265 grams (2.5 moles) of diethylene glycol, 320 grams (10.0 moles) of methanol, and 14.3 grams (0.0125 equivalents) of NAFION® 1100 EW Polymer (H$^+$ form) were charged to a one liter autoclave. After sealing and pressure testing, the contents of the autoclave were agitated and the autoclave was pressurized to 100 psi with nitrogen. After 5 minutes of agitation, the autoclave was depressurized. This process was repeated two more times to assure complete deoxygenation.

After deoxygenation, the autoclave was heated to a temperature of 198° C. and the contents of the autoclave were agitated at 1900 rpm for 5 hours at temperature (198–200° C.). A pressure of 810 psi was obtained. After 5 hours, the autoclave was cooled and sampled.

By analysis, a total of 77.2% by weight of the diethylene glycol (1.93 moles) was converted in the reaction, producing 0.335 moles of diglyme, 0.385 moles of co-product 1,4 dioxane, and 0.99 moles of the intermediate diethylene glycol monomethyl ether for a combined yield of 68.4% and selectivity of 88.6%.

EXAMPLE 3

A feed solution consisting nominally by weight of 2.4% of NAFION® 1100 EW Polymer (H$^+$ form), 12.7% ethylene glycol monomethyl ether, 20.7% ethylene glycol, and 64.2% methanol was continuously added to a one-liter autoclave containing a monoglyme batch prepared as described in Example 1. The feed solution was prepared by adding fresh ethylene glycol and methanol to the effluent obtained from previous autoclave batches (prepared as described in Example 1), which had been processed by distillation to separate monoglyme product, side-products, water and dimethylether from the reaction mixture.

Using a high-pressure pump, the feed solution was added at a rate equivalent to ⅕ of the reactor's working volume per hour (e.g., about 2.16 ml/min) into the autoclave mixture, which was kept at 200° C. and agitated at 1900RPM. The pressure was typically between 700 and 1000 psi. Material was removed at a rate of approximately 65 ml every 30 minutes.

Thus, over a period of about 82 hours, a total of about 1724 g (27.8 moles) of ethylene glycol, 1269 g (16.7 moles) of ethylene glycol monomethyl ether, and 4627 g (144.6 moles) of methanol were added to the reactor. By analysis, it was determined that about 8.5 moles of ethylene glycol dimethyl ether (monoglyme) and about 21.1 moles of ethylene glycol monomethyl ether were produced.

EXAMPLE 4

A feed solution consisting nominally by weight of 2.2% of NAFION® 1100 EW Polymer (H$^+$ form), 15.3% diethyleneglycol monomethyl ether, 33.7% diethylene glycol, and 48.4% methanol was continuously added to a one-liter autoclave containing a diglyme batch prepared as described in Example 2. This feed solution was prepared by adding fresh diethylene glycol and methanol to effluent obtained from previous autoclave batches (prepared as described in Example 2), which had been processed by distillation to separate diglyme,1,4 dioxane co-products and side-products, water and dimethylether from the reaction mixture.

Using a high-pressure pump, the feed solution was added at a rate equivalent to ⅓ of the reactors working volume per hour (e.g., about 2.12 ml/min) into the autoclave mixture, which was kept at 200° C. and agitated at 1900RPM. The pressure was typically between 700 and 1000 psi. Material was removed at a rate of approximately 64 ml every 30 minutes.

Thus, over a period of about 82 hours, a total of about 1724 g (27.8 moles) of ethylene glycol, 1269 g (16.7 moles) of ethylene glycol monomethyl ether, and 4627 g (144.6 moles) of methanol were added to the reactor. By analysis, it was determined that about 8.5 moles of ethylene glycol dimethyl ether (monoglyme) and about 21.1 moles of ethylene glycol monomethyl ether were produced.

Thus, over a period of about 80 hours, a total of about 2883 g (27.2 moles) of diethylene glycol, 1476 g (12.3 moles) of diethyleneglycol monomethyl ether, and 4269 g (133.4 moles) of methanol were added. By analysis, it was determined that about 5.8 moles of diethylene glycol dimethyl ether (diglyme), 2.3 moles of diethyleneglycol monomethyl ether and 6.4 moles of 1,4 dioxane were produced.

Additional advantages and modifications will readily occur to those skilled in the art. Therefore, the invention in its broader aspects is not limited to the specific details and illustrative examples shown and described herein. Accordingly, various modifications may be made without departing from the spirit or scope of the general inventive concept as defined by the appended claims and their equivalents.

What is claimed is:

1. A method of producing a glyme comprising contacting a glycol with a monohydric alcohol in the presence of a polyperfluorosulfonic acid resin catalyst under conditions effective to produce the glyme.

2. The method according to claim 1 wherein the glycol comprises diethylene glycol and the monohydric alcohol comprises methanol.

3. The method according to claim 2 wherein the glyme comprises diethylene glycol dimethyl ether.

4. The method according to claim 2 wherein the glyme comprises diethylene glycol monomethyl ether.

5. The method according to claim 1 wherein the glycol comprises diethylene glycol and the monohydric alcohol comprises ethanol.

6. The method according to claim 5 wherein the glyme comprises diethylene glycol diethyl ether.

7. The method according to claim 5 wherein the glyme comprises diethylene glycol monoethyl ether.

8. The method according to claim 1 wherein the glycol comprises ethylene glycol and the monohydric alcohol comprises methanol.

9. The method according to claim 8 wherein the glyme comprises ethylene glycol dimethyl ether.

10. The method according to claim 8 wherein the glyme comprises ethylene glycol monomethyl ether.

11. The method according to claim 1 wherein the glycol comprises ethylene glycol and the monohydric alcohol comprises ethanol.

12. The method according to claim 11 wherein the glyme comprises ethylene glycol diethyl ether.

13. The method according to claim 11 wherein the glyme comprises ethylene glycol monoethyl ether.

14. The method according to claim 1 wherein the glycol comprises triethylene glycol and the monohydric alcohol comprises methanol.

15. The method according to claim 14 wherein the glyme comprises triethylene glycol dimethyl ether.

16. The method according to claim 14 wherein the glyme comprises triethylene glycol monomethyl ether.

17. The method according to claim 1 wherein the glycol comprises diethylene glycol and the monohydric alcohol comprises 1-butanol.

18. The method according to claim 17 wherein the glyme comprises diethylene glycol dibutyl ether.

19. The method according to claim 17 wherein the glyme comprises diethylene glycol monobutyl ether.

20. The method according to claim 1 wherein the glycol comprises tetraethylene glycol and the monohydric alcohol comprises methanol.

21. The method according to claim 20 wherein the glyme comprises dimethoxytetraglycol.

22. The method according to claim 20 wherein the glyme comprises methoxytetraglycol.

* * * * *